(12) United States Patent
Rida

(10) Patent No.: US 8,585,279 B2
(45) Date of Patent: Nov. 19, 2013

(54) DEVICE AND METHOD FOR MANIPULATING AND MIXING MAGNETIC PARTICLES IN A LIQUID MEDIUM

(75) Inventor: Amar Rida, Chavannes-Renens (CH)

(73) Assignee: Spinomix S.A., Luasanne (CH)

( * ) Notice: Subject to any disclaimer, the term of this patent is extended or adjusted under 35 U.S.C. 154(b) by 675 days.

(21) Appl. No.: 12/340,069

(22) Filed: Dec. 19, 2008

(65) Prior Publication Data

US 2010/0157724 A1    Jun. 24, 2010

Related U.S. Application Data

(63) Continuation-in-part of application No. PCT/IB2007/052410, filed on Jun. 21, 2007, and a continuation-in-part of application No. PCT/IB2007/052409, filed on Jun. 21, 2007, and a continuation-in-part of application No. PCT/IB2006/054182, filed on Nov. 9, 2006, and a continuation-in-part of application No. PCT/IB2006/052005, filed on Jun. 21, 2006.

(51) Int. Cl.
 *B01F 13/08* (2006.01)

(52) U.S. Cl.
 USPC ...... 366/273; 366/274; 366/241; 422/186.01; 422/129

(58) Field of Classification Search
 USPC .............. 366/273, 274, 341; 422/186.01, 129
 See application file for complete search history.

(56) References Cited

U.S. PATENT DOCUMENTS

| | | | |
|---|---|---|---|
| 3,892,908 A | * | 7/1975 | Lovness ...................... 428/329 |
| 4,230,685 A | | 10/1980 | Senyei et al. | 
| 4,554,088 A | | 11/1985 | Whitehead et al. |
| 4,628,037 A | | 12/1986 | Chagnon et al. |
| 6,231,760 B1 | | 5/2001 | Siddiqi |
| 6,764,859 B1 | | 7/2004 | Kreuwel et al. |

(Continued)

FOREIGN PATENT DOCUMENTS

| EP | 0504192 B1 | 11/1994 |
|---|---|---|
| WO | WO-2006056579 A2 | 6/2006 |

OTHER PUBLICATIONS

Suzuki, Hiroaki and Chih-Ming Ho. "A Magnetic Force Driven Chaotic Micro-Mixer". The Fifteenth IEEE International Conference on Micro Electro Mechanical Systems, 2002.

(Continued)

*Primary Examiner* — Joseph Del Sole
*Assistant Examiner* — Nahida Sultana
(74) *Attorney, Agent, or Firm* — Mintz Levin Cohn Ferris Glovsky and Popeo, P.C.; Ivor R. Elrifi; Christina K. Stock, Esq.

(57) ABSTRACT

A device for manipulating and mixing magnetic particles (3) in a surrounding liquid medium, comprises at least one couple of magnetic poles (1,1') facing each other across a gap, the facing poles diverging from a narrow end of the gap to a large end of the gap, the poles (1,1') forming part of an electromagnetic circuit and being arranged to provide a magnetic field gradient in the gap region; and a reaction chamber (2) that is a part of a fluidic network for containing the said magnetic particles in suspension and placed in the gap of the said electromagnets poles (1,1'). The reaction chamber (2) preferably has at least one part which has a diverging cavity, arranged co-divergently in the diverging gap between the poles.

12 Claims, 12 Drawing Sheets

(56) References Cited

U.S. PATENT DOCUMENTS

| | | | |
|---|---|---|---|
| 7,632,405 B2* | 12/2009 | Siddiqi | 210/222 |
| 8,088,285 B2* | 1/2012 | Siddiqi | 210/695 |
| 8,114,353 B2* | 2/2012 | Benham et al. | 422/131 |
| 8,122,956 B2* | 2/2012 | Shammai et al. | 166/264 |
| 8,128,277 B2* | 3/2012 | Meier | 366/273 |
| 2004/0166547 A1 | 8/2004 | Sullivan et al. | |
| 2005/0032051 A1 | 2/2005 | Hayes et al. | |
| 2005/0208464 A1 | 9/2005 | Rida et al. | |
| 2006/0126429 A1 | 6/2006 | Coville et al. | |
| 2006/0133954 A1* | 6/2006 | Schroeder et al. | 422/61 |
| 2006/0140051 A1 | 6/2006 | Kim et al. | |
| 2006/0207944 A1* | 9/2006 | Siddiqi | 210/695 |
| 2011/0205835 A1* | 8/2011 | Zwirner | 366/273 |

OTHER PUBLICATIONS

Fan, Z. Hugh et al. "Dynamic DNA Hybridization on a Chip Using Paramagnetic Beads". Analytical Chemistry vol. 71; Nov. 1999.

Rida, A. et al. "Manipulation of Self-Assembled Structures of Magnetic Beads for Microfluidic Mixing and Assaying". Analytical Chemistry vol. 76; Nov. 2004.

* cited by examiner (a) Prior Art    (b) Prior Art (a)    (b)

DEVICE AND METHOD FOR MANIPULATING AND MIXING MAGNETIC PARTICLES IN A LIQUID MEDIUM

REFERENCE TO RELATED APPLICATIONS

This application is a continuation-in-part of International Application No. PCT/IB2007/052409 filed on 21 Jun. 2007, is a continuation-in-part of International Application No. PCT/IB2007/052410 filed on 21 Jun. 2007, International Application No. PCT/IB2006/052005 filed on 21 Jun. 2006, and is a continuation-in-part of International Application No. PCT/IB2006/054182 filed on 9 Nov. 2006, which are incorporated by reference herein.

FIELD OF THE INVENTION

The invention relates to a system of handling and mixing magnetic particles within a reaction chamber that is a part of a fluidic or microfluidic platform. More particularly, the invention concerns a method of handling magnetic particles in a way to improve the mixing of the particles with the surrounding liquids medium and where the liquids are automatically handled in a fluidic platform. Further, the invention relates to a method for conducting assays on a test sample containing specific biological or chemical substances using active biochemically surface magnetic particles and where the particles are handled following the foregoing system and method.

DESCRIPTION OF RELATED ARTS

Nowadays, magnetic particle (bead) is a standard technology in biochemical assays and diagnostics. Magnetic particle technology is indeed a robust technology that allows achieving high performances (sensitivity and accuracy) and also opens the possibility of easy automation of assay protocols. For many applications, the surface of magnetic particles is coated with a suitable ligand or receptor, such as antibodies, lectins, oligonucleotides, or other bioreactive molecules, which can selectively bind a target substance in a mixture with other substances. Examples of small magnetic particles or beads are disclosed in U.S. Pat. No. 4,230,685, U.S. Pat. No. 4,554,088 and U.S. Pat. No. 4,628,037.

One key element in magnetic particles bio-separation and handling technology is an efficient mixing to enhance the reaction rate between the target substances and the particle surfaces. Indeed, as for any surface-based assay the reaction is strongly limited by the natural diffusion process, a strong steering and mixing is necessary to promote the affinity binding reaction between the ligand and the target substance.

A typical example of magnetic particles mixing apparatus in test medium is disclosed in U.S. Pat. No. 6,231,760 and commercially available by Sigris Research Inc under the name of MIXSEP™ system. In this patent and system, the test medium with the magnetic particles in a suitable container are placed in a magnetic field gradient generated by an external magnet. The mixing concept is based on either the movement of a magnet relative to a stationary container or movement of the container relative to a stationary magnet using mechanical means, therefore inducing a "relative displacement" of the magnetic gradient position within the container. This magnetic field gradient displacement will in turn induce the magnetic particles to move continuously with the change of the magnet (magnetic field gradient) position, thereby effecting mixing. However, with this method the magnetic field gradient will attract and confine the particles in a cavity region close to the walls of the container. In such condition, the contact between the particles and the test medium is limited to the said cavity space which reduces the mixing efficiency. Although the "mechanical movement" of magnets is claimed as a mixing means, also described is the possibility of producing angular movement of the particles by sequential actuation of electromagnets disposed around the container. However, while electromagnets provide a much lower magnetic field when compared with permanent magnets, as described the magnetic coupling between adjacent electromagnets strongly repel the magnetic flux outside the container resulting in a further reduction of the magnetic field intensity and intensification of the cavity effect. Under such condition, the particles agitation (movement) and mixing will be strongly altered leading the particles to slowly move, mostly, as aggregates at the region close the walls border.

Within the same spirit, in the U.S. Pat. No. 6,764,859 a method of mixing magnetic particles in a container is disclosed based on relative "mechanical" movement between the container and intervening array geometry of magnet. In such configuration the adjacent magnets have opposite polarity which induces a change of magnetic field polarity during the relative intervening movement between the container and two adjacent magnets. In such conditions indeed, the particles can be moved while relatively separated from each other, which will potentially affect the mixing. However, in this approach when one takes in consideration the whole duration of the particles handling process, the time during which the particles are relatively separated from each other is relatively short. As a consequence, several mixing cycles are necessary to assure effective mixing. Moreover, during the mixing process the particles are not homogenously contacted with the sample volume in the test tube, which will in turn strongly limit the mixing efficiency. This issue is more pronounced as the sample volume is large.

Consequently when these mechanical mixing approaches are compared with the "manual shaking of a test tube", the reaction time and the performance are substantially similar if not lower, indicating that diffusion is still an important limiting factor.

Other aspects for magnetic particles separation and resuspending are disclosed in E.P, Pat 0,504,192. This patent discloses the use of sequential actuation of two magnetic field sources (electromagnets) disposed opposite to each other at the walls of a chamber. The proposed actuation concept of the said electromagnets is based on sequential energizing (actuation) of the electromagnets by "binary" (i.e., on and off) or "analog" in which a first electromagnet is gradually fully energized, and then has its power reduced, while the next electromagnet is gradually energized, and so on. Through this actuation the particles will be moved and drawn to the reaction chamber volume and thereby resuspended. While the concept of using (at least) two electromagnets with "sequential" actuation is conceptually an evident manner for particles resuspension from an aggregate, during their "movement" the particles remain mostly agglomerated due to their dipolar interaction under the applied magnetic field. The only way, after moving the "super-paramagnetic" particles to occupy the chamber volume, to fully assure "homogenous" resuspension in the chamber is to completely remove the external magnetic field and leave the desegregation to Brownian and thermal agitations. Additionally, the application discloses that alternately energizing and de-energizing the two electromagnets at a sufficiently rapid rate keeps the particles suspended in the center of the chamber. This process limits the movement of the particles to a relatively small distance, significantly reducing the mixing efficiency between particles and the surrounding liquid medium.

In general, beyond the limited mixing capability of the state of the art magnetic particles technologies, mainly based on the concept of "bringing a magnet in the proximity of a test tube", the integration and the automation of magnetic particles assay procedures are very complex, necessitating bulky robotic systems. These limitations become all the more critical as the assay procedures are becoming more and more complex.

Microfluidics based technology is nowadays perceived as an emerging technology with a great potential that can lead to easier integration of complex bio-chemical assay procedures in an easy-to-use and miniaturized automated system. Combining magnetic particles technology with microfluidics will certainly be of great importance as the precise control of different reagents (allowed by microfluidics) and handling of biological species and their reactions (allowed by magnetic particles) will be integrated together within a single system.

One approach of mixing magnetic particles in a microfluidics channel is taught in the publication "*Magnetic Force Driven Chaotic Micro-Mixer*", by Suzuki, H, in the proceedings of The Fifteenth IEEE International Conference on Micro Electro Mechanical Systems, 2002. The approach consists in flow mixing of magnetic particles injected in suspension in a microfluidic channel and where the mixing with the surrounding medium is assured by a magnetic field generated by embedded micro-electromagnets along the flow path. The combination of the magnetic force induced by the micro-electromagnets on the particles along with the flow driving force in the microchannel induces a chaotic regime and thereby mixing. A similar concept has been recently disclosed in U.S. patent application number 2006/140,051 where the magnetic field is generated by electromagnets disposed on the sidewalls in a predetermined direction with respect to the direction of the flow. By turning off/on the electromagnets in sequential operation, a rotating magnetic force can be created leading to mixing of the particles carried by the flow. The major limitation of this "in flow mixing" approach is that the volume of the test medium that can be mixed with the particles is very small and the reaction time very short, limiting considerably the cases of its applicability.

To overcome the limitations of the "in-flow mixing approach", a solution consists in retaining the particles in a given location of a fluidic channel or chamber using a magnetic field gradient while the test medium is injected with a flow through the retained magnetic particles. This approach has been disclosed in the U.S. patent applications number 2005/032,051 and 2004/166,547 where the particles retained in a flow microchannel have been used as a solid support for immunoassay procedures. Along the same lines, a flow-through concept applied for DNA hybridization and detection assay is described in the publication: "*Dynamic DNA hybridization on a Chip Using Paramagnetic Beads*", by Z. Hugh Fan & al., Analytical Chemistry, 71, 1999. However the so described flow-through approach suffers from a serious physical constraint, since in order to be handled in an environment with continuous fluidic processing, the particles must be continuously exposed to a magnetic field. Under such conditions the particles will stick together and agglomerate thereby losing their main advantage: the particle surface that is in active contact with the fluid flow will be drastically reduced which will seriously compromise the assay performance.

A solution to the agglomeration problem of magnetic particles in the flow-through approach has been disclosed U.S. patent application 2005/208,464. In this approach, the particles are retained in a portion of a flow-channel to form a kind of a filter that substantially homogenously covers the flow-channel cross section. To obtain this filter, the magnetic particles are manipulated using a time-varying field (amplitude, frequency and polarity) to control the particles agglomeration. The efficiency of this approach for microfluidic mixing of liquids has been demonstrated in a publication from the same author group "*Manipulation of Self-Assembled Structures of Magnetic Beads for Microfluidic Mixing and Assaying*", by A. Rida & al. Analytical Chemistry, 76, 2004. Even demonstrating an important development in magnetic particles handling and mixing in a microfluidic environment, the approach disclosed in U.S. patent application 2005/208,464 suffers however from many practical limiting constraints. First, as the particles are kept stationary and fixed in a narrow segment of the flow-through cell, the contact between the particles and the target substance is limited to that narrow region and for a very short time, which in practice makes such process difficult to set up. Secondly, this approach is specifically adapted for handling and mixing magnetic particles under flow-through conditions in microfluidics environments, which make it not fully adapted for different assay conditions.

The applicable known procedures and approaches have shortcomings, including the requirement for handling and mixing magnetic particles in various environments with more focus on microfluidics, as well various process constraints, limiting factors and inefficiencies.

SUMMARY OF THE INVENTION

The present invention provides devices and methods for handling and efficiently mixing magnetic particles in fluidic environments and more particularly in microfluidics environments. "Mixing" in the present context means in particular contacting in a very efficient manner large particles surfaces with the surrounding liquid medium, in such a way as to achieve: (1) an effective binding of the particles to a certain target molecule(s) and (2) further possibilities to wash, separate, elute and detect the targets captured on the particles from the residual liquid medium.

The proposed mixing mechanism provides a considerable and perpetual increase of the active surface of particles par unit of volume leading to an enhanced contact between this large surface of particles and the target substances. Further, the proposed magnetic particles handling process advantageously assures a homogenous mixing covering substantially the whole reaction volume in a fraction of time allowing thereby much more sample volume to be effectively and rapidly contacted with the particle surfaces. Moreover, during their manipulation the particles are in perpetual effective movement covering the whole reaction chamber volume, which is a key in enhancing particles mixing.

Further, the invention provides new devices and methods that practically allow the integration of complex assay procedures in a compact and easy to use system that can operate under flow-through or, advantageously, under non flow-through conditions.

A main aspect of the invention concerns a device and a method for manipulating and mixing magnetic particles, particularly in a microfluidics environment, attained according to independent claim 1.

Moreover, the invention discloses a microfluidic structure and composition that in particular integrate technical aspects related to the said device and method for manipulating and mixing magnetic particles. This aim is attained with a microfluidic chip according to the independent claim 13.

Different embodiments are set out in the dependent claims and another aspect of the device for manipulating and mixing magnetic particles in set out in any of the previous claims.

Different embodiments are set out in the dependent claims.

According to one embodiment of the present invention, : a device for mixing magnetic particles in a surrounding liquid medium and separating magnetic particles from a liquid medium, comprising:

(a) at least one couple of magnetic pole facing each other across a gap, the facing poles diverging from a narrow end of the gap to a large end of the gap, the poles with the gap are otherwise part of a preferably closed electromagnetic circuit arranged to provide a magnetic field gradient in the said gap region;

(b) a reaction chamber that is a part of a microfluidic network for containing the said magnetic particles in suspension and placed in the gap of the said electromagnets poles, wherein the reaction chamber has inlet/outlet ends for introducing and removing the liquid medium into and from the reaction chamber, the reaction chamber extending between its ends along said gap such that the ends of the reaction chamber are in correspondence with the narrow and large ends of the gap.

(c) wherein preferably each of magnetic poles actuated with a magnetic field sequences having polarity and amplitude that vary in time to induce time variations of the position of the magnetic field gradient maxima across the reaction chamber, causing thereby the particles in use to be in relative translational and rotational motion as a fog of particles covering the whole reaction chamber volume.

One key element of this device according to the invention is the variation of the geometry of the reaction chamber expressed herein by a transverse increase of the channel dimensions (converging parts) or a decrease in the channel's dimensions (diverging parts). Such variation of the channel geometry will induce flow velocity variation across the reaction chamber cross-section, which is a key factor of the disclosed mixing mechanism. In fact, contrary to a channel with a uniform geometry where the flow stream is developed only in a direction normal to the principal channel cross-section, variations of the microchannel geometry will induce transverse velocity gradients leading to a more effective flow mixing.

Accordingly, the variable-geometry reaction chamber is placed in an air gap between magnetic poles that have shapes that vary in the same direction as the geometry of the reaction chamber. The diverging/converging parts of the reaction chamber are placed in the air gap of at least one couple of magnetic poles facing each other across a gap and where the said magnetic poles are arranged co-divergently/co-convergently with the reaction chamber's diverging/converging parts. The converging/diverging arrangement of magnetic poles will induce a variation of the magnetic field across the air gap region delimited by the magnetic poles, creating thereby a magnetic field gradient covering the whole volume of the reaction chamber placed in the said pole's air-gap. The so-generated magnetic field gradient serves as a driving force for magnetic particles manipulation and mixing in the reaction chamber.

The desired effect obtained by the so-described reaction chamber/magnetic poles geometries is that the magnetic field gradient variation profile corresponds to the same variation profile as for the flow velocity gradient in the reaction chamber. Such "co-variation" of the flow velocity/magnetic field gradients (forces) allows to: (1) retain and separate the said magnetic particles in the reaction chamber under a fluid flow conditions and (2) achieve more homogeneity in the mixing conditions (and therefore more controlled and efficient mixing) of the magnetic particles with the surrounding liquid medium.

Another key aspect of the present invention concerns the magnetic poles actuation mechanism which consists of:

(1) applying from the electromagnetic poles magnetic field sequences having polarity and intensity that vary in time; said varying magnetic field sequences being effective to break or inhibit particle claim aggregates and to maintain the particles in suspension as a fog of particles in relative dynamic motion; and (2) combining the magnetic fields from different magnetic poles in a sequence to induce displacement of the fog of particles across the reaction chamber whereby the fog of particles occupies substantially the whole reaction chamber volume quasi-instantaneously or over a period of time.

It has been found that this mechanism of magnetic poles actuation leads to continuous time variations of the position (displacement) of the magnetic field gradient maxima across the reaction chamber volume, leading thereby the particles to be in perpetual relative translational and rotational motion that can substantially cover the whole reaction chamber volume.

Additionally, the desired effect obtained by the actuation mechanism according to the invention is that during their motion the particles do not displace as a compact aggregate but they are rather moving as a fog of particles resulting in a strong enhancement of the contact between the of particles surfaces and the surrounding liquid medium.

Additionally, the desired effect obtained by the actuation mechanism according to the invention is that the particles mixing will cover substantially the whole reaction chamber volume and not be limited to a narrow segment as in the disclosed prior art concepts. This magnetic particles handling process advantageously assures therefore a homogenous mixing allowing much more liquid volume to be effectively contacted with the particle surfaces.

Additionally, the desired effect obtained by the actuation mechanism according to the invention is the possibility of selecting the magnetic field sequence to not only homogenously mix the particles but also separate or confine the particles so the particles occupy a sub-volume in the volume of the reaction chamber at the outer borders of the reaction chamber. For instance one can apply a first magnetic field sequence to homogenously displace and therefore mix the particles in substantially the whole reaction chamber volume; and then apply a second magnetic field sequence that specifically selects the direction of the magnetic field gradient leading the particles to be drawn to a sub-volume of the reaction chamber determined by the direction of the applied magnetic field gradient. This flexibility in controlling the particles is advantageously important as it allows to handle and control the particles' state in correspondence with the assay process.

Another feature of the invention is that during their perpetual motion (movement) the size of the particles aggregates can be mainly controlled by the "frequency" of the magnetic field polarity variations while the homogeneity of mixing is controlled by the magnetic field amplitude. Accordingly, the magnetic field (gradient) amplitude can be used as a switching parameter to, for instance, homogenously mix the particles over the substantially the entire volume of the reaction chamber or draw (separate) them to the outer border of the reaction chamber.

Additionally, a desired effect obtained by the device and the actuation mechanism according to the invention, is the extremely fast manipulation of the particles. For instance, starting from a configuration where the particles are first separated to the outer border of the reaction chamber using a specific first actuation sequence, a fraction of time (a second or less) is sufficient to put the particles in a homogenous mixing configuration using a second actuation sequence. The particles can afterwards again be drawn in a fraction of time to the outer border of the reaction chamber by applying the first actuation sequence. This rapid manipulation process can be even reached in a complex high viscous medium like blood lysate.

To reach the desired effects, the magnetic particles in use are preferably initially unmagnetized magnetic particles that develop a specific ferromagnetic hysteresis response to an external magnetic field. More specifically, the particles have a coercive field between 200 to 1000 Oe.

To reach the desired effects, the time varied magnetic field sequences preferably have, sinusoidal, saw-tooth, asymmetrical triangular, or symmetric triangular form, or any combination of these forms.

According to the invention, a microfluidic chip comprises:
  (a) a reaction chamber that is a part of a fluidic network, having at least one cavity with diverging-converging parts
  (b) opening placed on both sides of the reaction chamber to receive magnetic poles that are part of an external magnetic circuit, and wherein
  (c) the magnetic poles are geometrically arranged in a way to be co-diverging/co-converging with diverging-converging parts of the reaction chamber.

According to the previously described aspects and effects, the present invention disclose a method of mixing magnetic particles in a microfluidic environment with surrounding medium in a reaction chamber that is a part a microfluidic network, wherein at least a couple of electromagnetic poles face each other across the reaction chamber, the method comprising:
  (a) applying a magnetic field sequences having polarity and intensity that vary in time from each of the electromagnetic poles,
  (b) combining the magnetic field from each magnetic pole to induce continuous time variations of the position of the magnetic field gradient maxima across the whole reaction chamber volume; and
  (c) causing the particles to be to be homogenously distributed and to dynamically move as a fog of particles over a substantial portion of the reaction chamber volume.

Regarding a final objective of the invention, the particles in use have a surface coating designed to allow affinity recognition with at least one target molecule or reaction with the surrounding liquid medium within the reaction chamber. The said target molecules or reagents are carried by a flow to the reaction chamber. When combined together, all aspects of the current invention allow the processing with enhanced performance of complex biochemical, synthesis and analysis procedures using magnetic particles as a solid support. Typical examples but without limitation of such procedures are enzymes-linked assay, proteins and nucleic acids extractions, or detection methods based on enzymatic signal amplification methodologies such as chemoluminescence, NASBA, TMA or PCR.

BRIEF DESCRIPTION OF THE DRAWINGS

The objects and features of the present invention are set forth with particularity in the appended claims. The present invention, both as to its organization and manner of operation, together with further objects and advantages, may best be understood by reference to the following description, taken in connection with the accompanying drawings, wherein FIGS. 1(a) and (b) are schematic representations of the concept of flow-through magnetic particle handling approaches as described in the prior art.

FIGS. (5)(a) and (b) are schematic representations of magnetic particle handling and mixing according to a preferred embodiment of the invention which includes in particular a change in the direction of the polarity of the magnetic poles, whose induced magnetic field has the effect of axially moving the particles.

DETAILED DESCRIPTION OF THE PREFERRED EMBODIMENTS

The main attainable effect of the present invention is an effective control of the magnetic particles that allows an enhanced and homogenous mixing with the surrounding medium. In particular, the mixing of the magnetic particles is realized in a reaction chamber that is a part of a micro-fluidic network and where the particles are handled using external magnetic poles with specific configurations and geometries. Accordingly, the different reagents are introduced to the reaction chamber using liquid flows and the magnetic poles are specifically actuated to control the magnetic particles in use inside the reaction chamber.

In general, the microfluidic environment of the invention concerns devices typically designed on a scale suitable to analyze micro-volumes preferably in the range 0.1 µl to 500 µl. However, in one of major application of the invention large samples are used to concentrate specific biomolecules in the device to a small volume for subsequent analysis. The microscale flow channels and wells have preferred depths and widths on the order of 0.05-1 mm. The "reaction chamber" that is part of a microfluidic network as used herein refers to chambers with a cavity that have a volume in the range of 0.1 µl to 500 µl and preferably in the range 10 µl to 100 µl. However, for many applications, larger "mesoscale" dimensions on the scale of millimeters may be used. Similarly, chambers in the substrates often will have larger dimensions than the microchannels, on the scale of 1-10 mm width and 1-5 mm depth.

Figure 1:
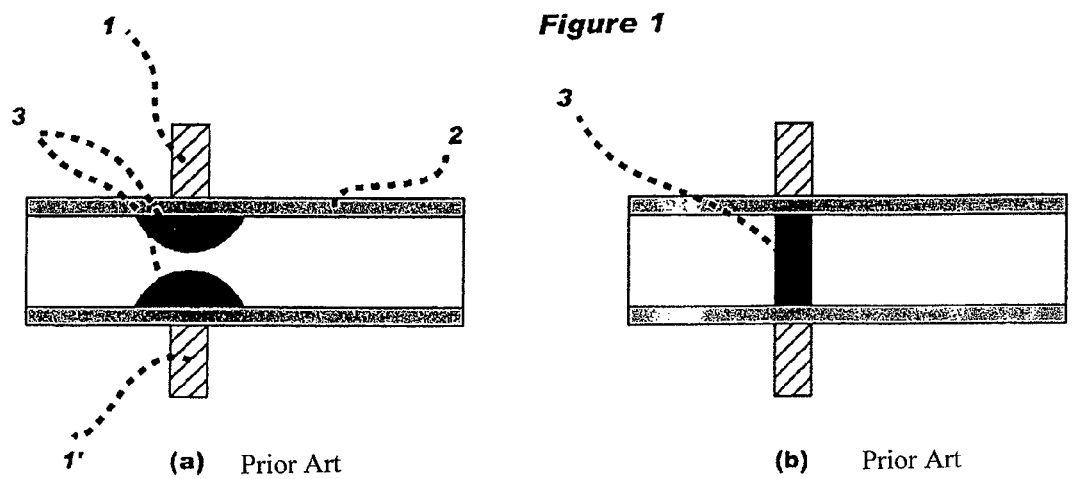

To illustrate the key advantage of the present invention, FIG. 1 schematically shows the concept of a flow-through magnetic particles handling approach as described in the prior art. In the prior art indeed, the particles (3) are kept fixed in a narrow region of a flow-through cell (2) delimited by magnetic pole tips (1) and (1'). The particles can partially cover the flow-through cell cross section (FIG. 1(a)) when a static field is applied as described in U.S. patent application 2004/166,547, or homogenously cover the flow cell cross section (FIG. 1(b)) when a time varied magnetic field is applied as described in U.S. patent application 2005/208,464. The pole tip configurations used to generate a magnetic field gradient confine the particles in a stationary fixed and narrow segment of the flow-through cell, which limits the contact between the particles and the target molecules to that narrow region and for a very short time.

Figure 2:
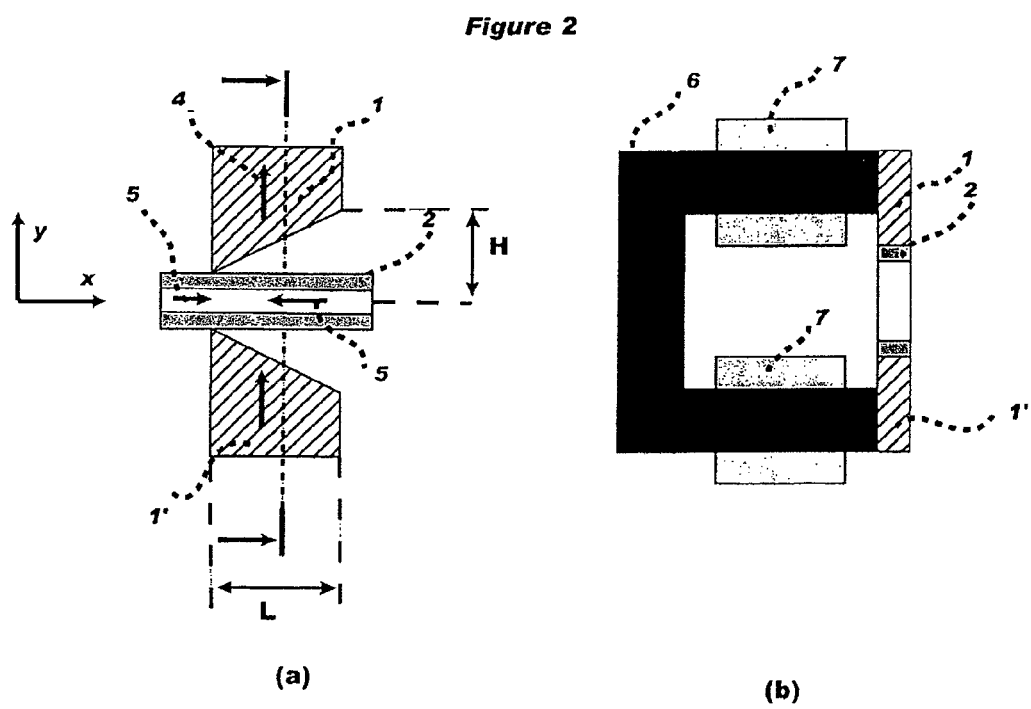
FIG. 2(a) shows a schematic view of one preferred embodiment of the invention which includes one couple of "diverging" magnetic poles facing each other across a gap and a reaction chamber (channel) placed in this gap.
FIG. 2(b) is a cross-sectional view of FIG. 2(a), showing in particular the electromagnetic circuit that provides the magnetic field in the reaction chamber.

To overcome the limitations of the prior art, a new magnetic device and magnetic pole geometry is disclosed. Accordingly, as shown in FIG. 2, a device for manipulating and mixing magnetic particles in a surrounding liquid medium, comprises: (i) at least one couple of magnetic poles (1)-(1') facing each other across a gap, the facing poles diverging from a narrow end of the gap to a large end of the gap. The poles form part of an electromagnetic circuit and are arranged to provide a magnetic field gradient (5) in the gap region. In this gap region is placed a tubular reaction chamber (2) that is a part of a fluidic network and in which the magnetic particles in use will be manipulated. The magnetic circuit is composed of a magnetic core (6) and coils (7) that when supplied with an electric current produce a magnetic field in the gap region through the magnetic poles (1), (1'). Moreover, each magnetic pole (1) and (1') is preferably electromagnetically actuatable independently from each other using two independently actuatable coils (7).

The effect obtained by the described magnetic pole geometry is that the magnetic field gradient will not be limited to a narrow region but will cover the whole space region extending along the axial X direction in the said poles air-gap.

To enhance the mixing effect, preferably the reaction chamber (2) placed in the air gap region has a cavity shape that varies in the same direction as the geometry of the magnetic poles. As schematically represented in FIG. 3(a), rather than having a flow channel with a uniform geometry (uniform cross-section) as in FIG. 2(a), the reaction chamber (2) has preferably a variable geometry that is substantially co-diverging in the diverging gap between the poles. With such variation of the reaction chamber geometry one will induce a transverse velocity gradient (8) leading to more effective flow mixing (see FIG. 4).

Figure 5:
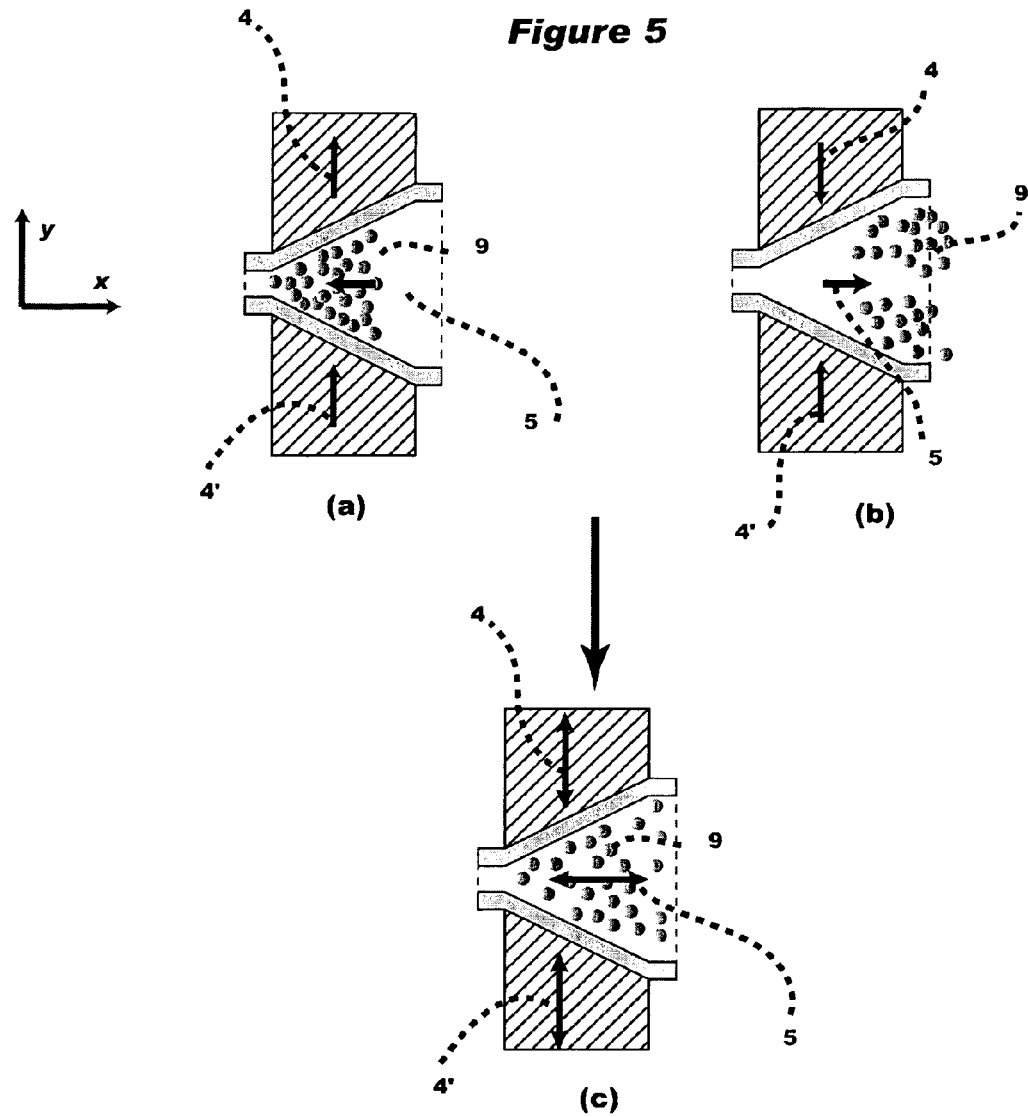
FIGS. 5 (c) is a schematic representation where the magnetic particles substantially homogenously cover ther whole reaction volume.

In operation, the space-varied magnetic field generated by the magnetic poles (1)-(1') provides a magnetic field gradient and thus a magnetic force (5) along the X direction that will be used to retain the magnetic particles (9) during the flow of a fluid in the reaction chamber (2) (see FIG. 5). In order to be able to retain the particles (9) in the reaction chamber (2), the generated magnetic force (5) acting on the particles must be greater than the flow drag force which tends to drive the particles away. Moreover, since the magnetic force (5) and the flow drag force decrease in the same way along the X direction, it will be possible to control the generated magnetic force (5) so that it is substantially equal to the flow drag force. When introduced in the reaction chamber (2) and subjected to a static magnetic field (5), the magnetic particles (9) tend to form magnetic chains along the magnetic field flow line. Due to the magnetic field gradient generated in the reaction chamber (2), the magnetic particle chains will coalesce to form a strongly aggregated chain-like structure. Preferably the amount of magnetic particles (9) used is such that the magnetic aggregated structure mostly located near the magnetic poles in the conical part of the reaction chamber (2), as shown in the left of FIG. 5(a). A time varied magnetic field as an alternating magnetic field is then applied to break down the aggregated chain-like structures with the fluid flow through such magnetic particle structures at a predefined flow rate (i.e. slightly increased, as necessary). A low aggregated magnetic structure is obtained, as illustrated in the right of FIG. 5, and controlled by adjusting the magnetic field amplitude and frequency, the magnetic field gradient provided by the pole geometry, and the fluid flow rate in the reaction chamber (2).

The desired effect obtained by the so-described reaction chamber/magnetic pole geometries is that the magnetic field gradient variation profile corresponds to the same variation profile as for the flow velocity gradient in the reaction chamber (as shown in FIG. 3(b) and FIG. 4(b)). Such "co-variation" of the flow velocity/magnetic field gradients (forces) allows to reach more homogeneity in the mixing conditions (and therefore more controlled and efficient mixing) of the magnetic particles with a liquid flow.

The geometrical parameter of the device of FIGS. 2 to 5 according the invention, must be set in a way to reduce the magnetic losses and assure a maximum focus of the magnetic flux in the reaction chamber (2). Moreover, the adjustment of these dimensions must be performed in a way that the generated magnetic field gradient covers the whole reaction chamber and minimizes the existence of zones inside the reaction chamber with a vanishing magnetic field gradient. In this perspective, ratio between the depth (H) of the large end to the length (L) of the diverging part of the reaction chamber is between 0.1 to 10 and preferably between 0.1 to 1. Typical values of the length (L) of the diverging parts are between 50 µm and 10 mm, preferably between 100 µm and 5 mm. The dimensions of the microfluidic channel connected to the narrow end of the reaction chamber are in the range of 50 µm to 5 mm and preferably between 100 µm and 1 mm.

Accordingly, a key aspect of the present invention concerns the magnetic poles actuation mechanism which is based on the application in each electromagnetic pole of magnetic field sequences having polarity and intensity that vary in time.

A typical example of this actuation aspect according to the invention is illustrated in FIG. 5. As schematically shown in FIG. 5(a), a "parallel oscillating" magnetic field (4)-(4') is applied to the magnetic poles:

$$\text{Poles 1 and 1'}: B = B_0 \sin(2\pi f_1 t) \quad (1)$$

under such condition and due to the perpetual change in the field polarity, the magnetic agglomeration (chains) will break down to smaller particles chain-like structures with a size that decreases with the field frequency ($f_1$). Ultimately, the particles will behave like a fog of particles in relative dynamic motion. Another important phenomenon characterizing the use of "oscillating" magnetic field, is the generation of negative dipolar interaction between the particles (due to the fact that the particles will not rotate at the same rate) that contribute further in the particles agglomeration break-up. For instance, contrary to the case of a static field where the particles will be mostly attracted as an aggregated mass toward the magnetic poles (as shown in FIG. 1(a)), in an oscillating magnetic field the particles (while rotating) tend to be homogenously distributed over the reaction chamber cross section (as shown in FIG. 5(a)). In other words, under an oscillating magnetic field the particles will tend to occupy a larger space due the development of repulsive magnetic forces between the particles.

In summary, the use of a magnetic field that has a polarity and amplitude that vary in time as a base actuation of the magnetic poles according to the invention allows for an effective breaking or inhibiting of particle aggregates and tends to maintain the particles in suspension as a fog of particles in relative dynamic motion.

However, as the manipulation of magnetic particles necessitates the use of magnetic (force) gradient (5), the particles will be attracted to the narrow segment of the reaction chamber, which will confine and therefore tend to agglomerate the particles. This agglomeration can be reduced by reducing the applied field amplitude ($B_0$) and thereby the magnetic force gradient. If in fact, one reduces the force by reducing applied field amplitude ($B_0$), one observes that the "rotating" particles structure (9) will expand radially along the X direction due to the repulsive magnetic forces between the particles induced by their relative rotation.

To overcome further agglomeration induced by the magnetic field gradient, according to the invention as shown in FIG. 5(b), the polarity of the magnetic field polarity (4)-(4') generated from each of magnetic poles (1) and (1') is changed from parallel to opposite (anti-parallel):

Pole 1: $B = B_0 \sin(2\pi f_1 t + \pi)$

Pole 1': $B = B_0 \sin(2\pi f_1 t)$ (2)

to cause a change in the direction of the magnetic force (5), which will move the particles (9) axially in the X direction, following the direction of the magnetic force (5), from the narrow segment to the large segment of the reaction chamber.

Accordingly, continuous "switching" between the two actuation schemes of the magnetic poles defined by equations (1) and (2) leads to continuous time variations of the position of the magnetic field gradient maxima from the narrow to the large segments of the reaction chamber. These magnetic field gradient maxima changes will in turn lead the particles to be in perpetual axial movement between the narrow and the large segments of the reaction chamber following the magnetic field gradient (5) variations.

Accordingly, the actuation mechanism according to the invention is based on the finding that by appropriate choice of the switch frequency ($f_2$) between the actuation scheme of the magnetic poles defined by equation (1) and (2), one can reach a state where the particles will substantially homogenously cover the whole reaction volume, as schematically shown in FIG. 5(c).

The so described actuation mechanism, leads the particles to be in perpetual relative translational and rotational motion that can substantially cover the whole reaction chamber volume. Such particles dynamics is the key factor in the disclosed particle mixing according to the invention, as the mixing will cover substantially the whole reaction chamber volume and not be limited to a narrow segment as in the disclosed prior art concepts. This magnetic particles handling process advantageously assures therefore a homogenous mixing allowing much more liquid volume to be effectively contacted with the particle surfaces.

Moreover, as when compared with the previous art magnetic particles resuspension concept of E.P, Pat 0,504,192, the use of sequential energizing (actuation) of the electromagnets by "binary" (i.e., on and off) or "analog" with the disclosed magnetic device of FIG. 2, leads the particles to move very slowly while remaining mostly agglomerated. Moreover, the polarity alteration between the two states of FIGS. 5(a) and 5(b) will not substantially solve this issue as suggested by the U.S. Pat. No. 6,231,760. Such difficulties are a specificity of "microfluidics" where the relatively "small" working volume leads to strong magnetic coupling between the adjacent magnets.

For solving this issue, the key finding of the present invention is to apply in each electromagnetic pole magnetic field sequences having polarity and intensity that vary in time, the role of which is to effectively break or control the particle aggregates and to maintain the particles in suspension as a fog of particles in relative dynamic motion; and then combining the magnetic fields from different magnetic poles in a sequence to induce homogenous mixing of the particles over substantially the whole reaction chamber volume.

For clarity, and contrary to what one could as a first view expect, the "arrows" representing the magnetic poles polarity in FIGS. 5(a) and 5(b) (and in all other Figures), are not fixed. In practice, these polarities are continuously changing direction in time. The "fixed" narrow direction, "instead", represents the "relative" polarization of the electromagnets during the particles manipulation.

Figure 6:
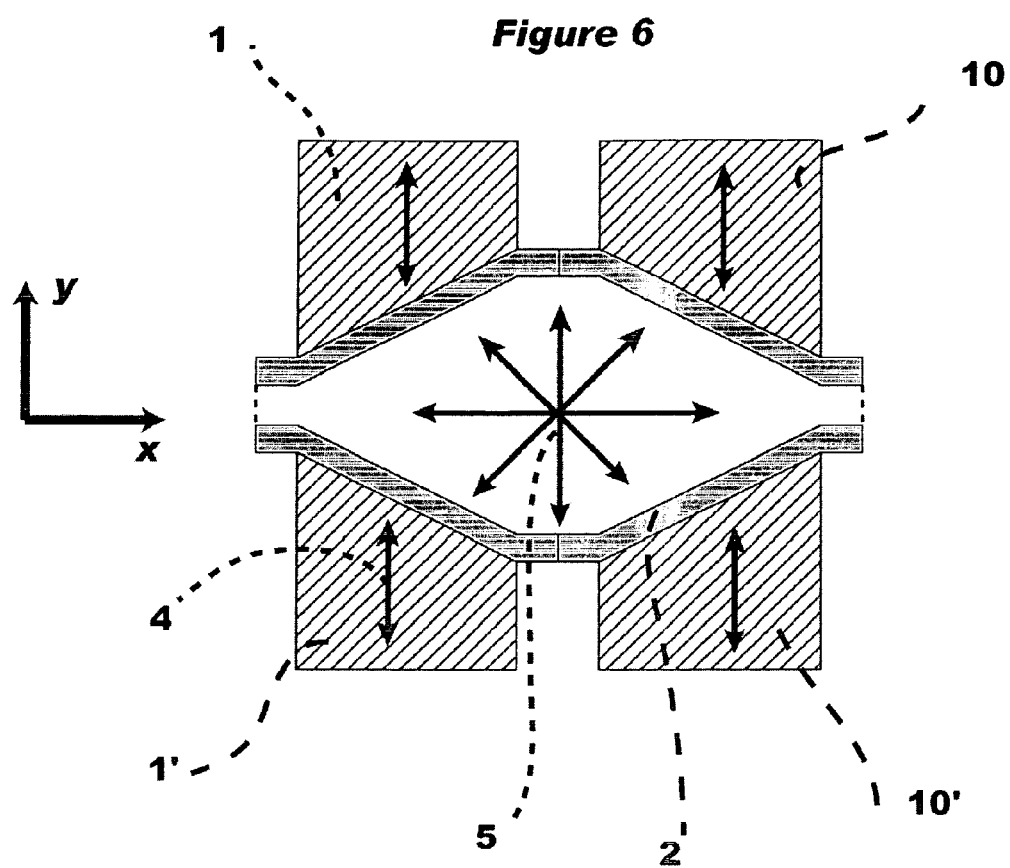
FIG. 6 shows a schematic view of yet another preferred embodiment of the invention which includes a quadrupole configuration of magnetic poles, co-diverging/co-converging with the reaction chamber cavity.

In another embodiment according to the invention and as shown in FIG. 6, a device for manipulating and mixing magnetic particles is provided where the magnetic poles form a quadrupole comprising (i) a first couple of magnetic poles (1)-(1') facing each other forming a diverging gap; and (ii) a second couple of magnetic poles (10)-(10') facing each other and forming a diverging gap, with the large ends of the diverging gaps of the first and second couples of poles facing one another; and (iii) a reaction chamber (2) that is a part of a fluidic network, having a cavity with diverging parts of the reaction chamber that are arranged co-divergently in the diverging gaps between the poles.

It is clear that the quadrupole configuration is a more sophisticated version of the previous embodiments allowing more enhanced effects. More specifically, the magnetic field gradient (5), rather than being substantially axial (axial symmetry) as in the case of the previously described two poles configuration, has a substantially "spherical symmetry". The possibility of having a "multi-directional" magnetic field gradient induced by more than a couple of magnetic poles, offers the possibility to move the position of the magnetic field gradient maxima following more "rich" configurations as shown in FIG. 7(a)-(e). In particular, by proper and sequential actuation of the magnetic field (4) induced from each magnetic pole of the multi-poles (quadrupole) configuration one can to move the position of the magnetic field gradient maxima across the reaction chamber volume in way that the sequential position of these maxima covers the whole reaction chamber volume.

FIGS. 7(a)-(e) schematically represent the different magnetic poles actuation (4) and the corresponding magnetic particles configurations, which correspond indeed to the position of the magnetic field gradient maxima. An effect obtained by such magnetic handling process is that by sequentially moving the particles, for instance, following the configuration of FIGS. 7(a)-(e), the particles movement will cover substantially the whole volume of the reaction chamber as shown in FIG. 8, thereby assuring a strong mixing with the surrounding liquid medium.

From what precedes, a first key element in the actuation mechanism according the invention is a "base" magnetic field actuation (4) of the magnetic poles which is a magnetic field with a polarity and amplitude that vary with time. A typical example of this actuation field is an oscillating magnetic field as the one of equation (1). In general, such base magnetic actuation field has a substantially rectangular, sinusoidal, saw-tooth, asymmetrical triangular or symmetric triangular form or any combination of such forms.

From what precedes, a second key element in the actuation mechanism according to the invention is that the magnetic poles are actuated following a certain sequence to induce continuous time variations of the position of the magnetic field gradient maxima across the whole reaction chamber volume, causing thereby the particles in use to be in relative dynamic motion covering the whole reaction chamber volume.

Accordingly, in the invention by "field sequences having polarity and intensity that vary in time" one means the composition of the "base" actuation field on each magnetic pole along with its sequential variation to induce the particles movement across the reaction chamber volume. In practice indeed, one can decompose the field sequences actuating each magnetic pole in two main components: (1) a base actuation field component that has a polarity and amplitude that vary with time and (2) a sequential variation of this base actuation field to induce the particles displacement across the reaction chamber and thereby affecting particles mixing.

Accordingly, in practice the base actuation field component will have the role of breaking the particles chains aggregates and thereby assure large surfaces of the particles to be in contact with the surrounding liquid medium while the sequential variation of this base actuation field will induce continuous move of the particles "fog" over the whole reaction chamber assuring thereby an homogenous exposure of the "disaggregated" particles over substantially the whole volume of the reaction chamber.

Consequently, a desired effect obtained by the actuation mechanism according to the invention is that during their motion the particles do not displace as a compact aggregate but they are rather moving as a fog of particles resulting in a strong enhancement of the contact between the of particles surfaces and the surrounding liquid medium.

In the previously described actuation mechanism, the time variation of the base actuation field as well as the sequence actuation of the magnetic poles is a non-periodic variation but it is preferably a periodic variation. In the periodic case, the frequencies of the base field ($f_1$) and the actuation sequence ($f_2$) can be in practice different ($f_1 \neq f_2$). To reach the previously described particle mixing effects, the actuation sequence frequency ($f_2$) is lower than or at most equal to the to base field frequency ($f_1$). In general, to reach the previously-described particle mixing effects the time field variation of the base field (i.e. the time variations of the amplitude and the polarity of in each magnetic pole) is preferably higher or at least equal to the sequential time actuation of the magnetic poles.

The time variations of the magnetic field in accordance with the invention, defined by the frequencies $f_1$ and $f_2$, is in the order of 0.1 Hz to 1000 Hz and preferably between 1 Hz and 500 Hz, or other time scales characterizing non-periodic variations.

An advantageous effect obtained by the actuation mechanism according to the invention is that particles will exhibit a dynamics movement that substantially covers the whole reaction volume over a certain period of time. According to the invention indeed, the particles will homogenously cover at least 60% of the reaction chamber volume and preferably between 80% and 99% of the reaction chamber volume. This homogenous coverage will be achieved in period of time that is determined by the sequence actuation time (or frequency) of the magnetic poles. In practice, the homogenous mixing is achieved in a period of time between 10 s and 10 ns and preferable 1 s and 10 ms. In preferred embodiments and depending on the actuation field parameters the homogeneity of mixing will cover 99% of the reaction chamber over time.

To reach the desired effects, the magnetic particles in use are preferably initially unmagnetized magnetic particles that develop a specific ferromagnetic hysteresis response to an external magnetic field. More specifically, the particles have a coercive field between 200 to 1000 Oe. Contrary to what is reported in the previous art where the particles in use are preferably "superparamagnetic", it has been found that the fact that the particles exhibit a specific (ferromagnetic) hysteresis response is a key condition to achieve the mixing effects according to the invention. In fact, as described before, the particles actuation mechanism consists in the use of a preferably a high frequency "oscillating" field as "base" actuation magnetic field component on each magnetic pole to control and break down the particles aggregates. At such high variation frequencies ($f_1 > 1$ Hz), the fact that the particles have hysteresis response allow them to follow such "rapid" field variations by physically rotating with the field oscillations. This particles rotation in a high frequency oscillating magnetic field (field having polarity and intensity that vary in time) is at the origin of the particles desegregation process.

Moreover, to reach the desired effects, it has been found that preferably the particles in use are manipulated with an "oscillating" (field having polarity and intensity that vary in time) magnetic field with an amplitude (maximum field strength) that is lower then the coercive field of the particles in use.

Accordingly, the particles in use preferably are synthesized with properties following the process disclosed in the patent application WO2006/056579, herein incorporated entirely as a reference.

In general the invention provides a method of integrating all of the previously described magnetic particles handling and mixing in microfluidic environment concepts. The method consists in the use of a reaction chamber that is a part a microfluidic network, wherein: at least one couple of electromagnetic poles face each other across the reaction chamber, the method comprising: (a) applying magnetic field sequences having polarity and intensity that vary in time from each of the electromagnetic poles, (b) combining the magnetic field from each magnetic pole to induce continuous time variations of the position of the magnetic field gradient maxima across the whole reaction chamber volume; and (c) causing the particles to be in relative translational and rotational motion covering the whole reaction chamber volume.

Figure 9:
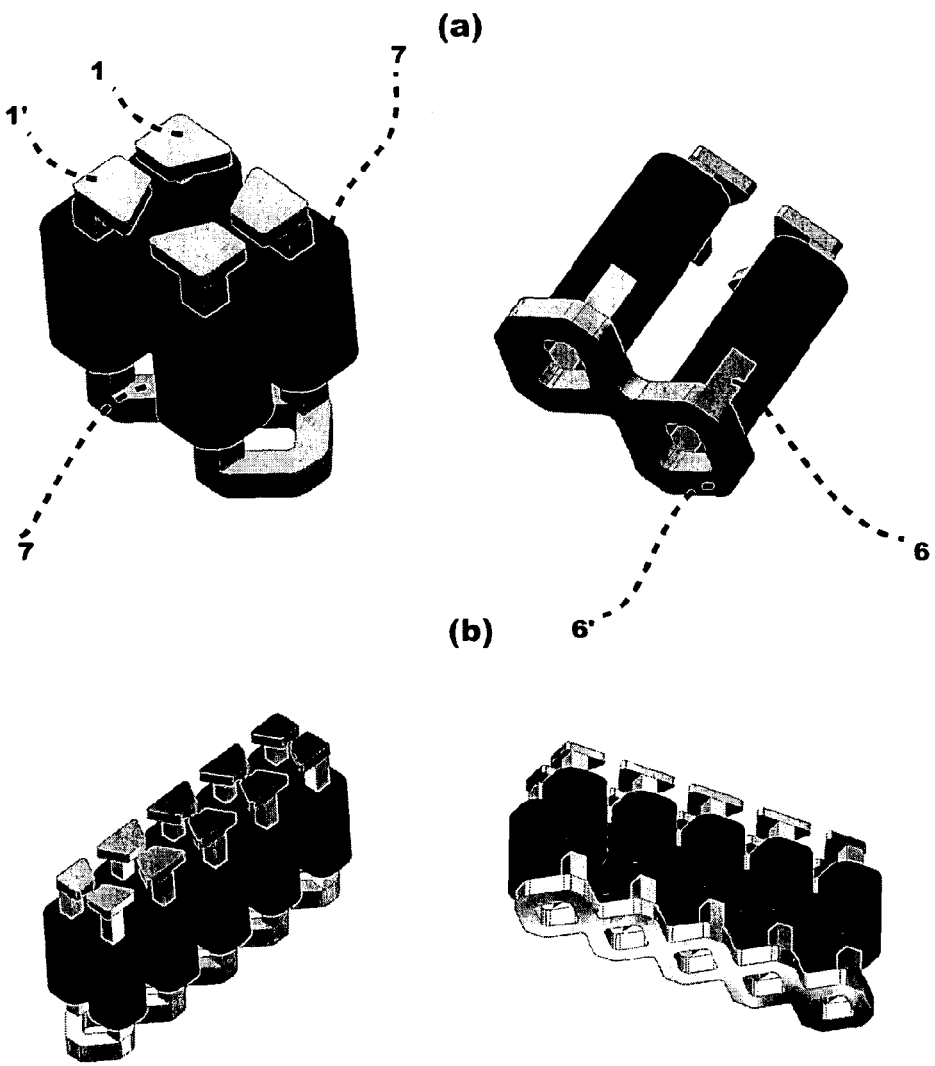
FIGS. 9(a) and (b) show a perspective view of the electromagnetic circuit according to a preferred embodiment of the invention.
Figure 10:
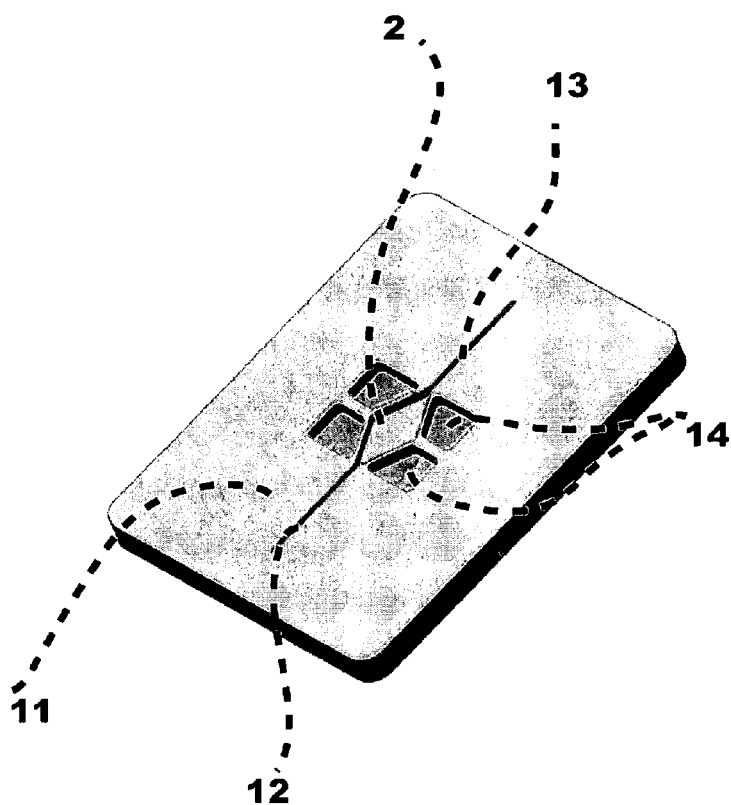
FIG. 10 show a layout of a microfluidic chip according to a preferred embodiment of the invention.

To obtain the desired effect, the magnetic poles are preferably magnetically coupled one to each other by a "closed" magnetic circuit. A typical example of such magnetic circuit is illustrated in the perspectives views of FIG. 9. Indeed as shown in FIG. 10(a), for the quadrupole configuration of FIG. 6, each magnetic pole (1)-(1'), (10)-(10') is connected to an electromagnet formed by a magnetic core (6) with a coil (7). Moreover, each magnetic core (6) is in contact with a "base" magnetic core part (6') in form of an "8". The "8" shape of the base magnetic core 6' assures that each magnetic pole pair configuration forms a closed magnetic circuit assuring thereby a stronger circulation of the magnetic flux during the actuation process like the one described by equation (1). Moreover, the fact that each pair of magnetic poles form a "closed" magnetic circuit is essential to strongly focus (concentrate) the magnetic flux and magnetic flux gradient in the reaction chamber. Moreover, this condition is particularly preferable to assure the mixing process and effects, in accordance with invention, as previously described.

FIG. 9(b) shows a more sophisticated form of the quadrupole configuration and magnetic circuit of FIG. 9(a), with an array of quadrupole configurations to assure parallel actuation and handling magnetic particles according to the invention in four different adjacent reaction chambers. The same design and construction of a quadrupole array can be extended for handling magnetic particles in a larger number of reaction chambers.

Another aspect of the invention is related to a microfluidic chip that integrates the different geometrical aspects of magnetic particles manipulation and mixing described above. Accordingly, a microfluidic chip comprises: (a) reaction chamber (2) that is a part of a fluidic network, containing the particles in use in suspension and having at least one cavity with diverging/converging parts, (b) inlet (12) and outlet (13) channels, for delivering liquids into and from the reaction chamber and connected respectively to the narrow segments of the diverging/converging parts, (c) an entries structure (14) placed on both sides of the reaction chamber (2) to receive magnetic poles that are part of an external magnetic circuit and wherein the magnetic poles are geometrically arranged in a way to be co-diverging/co-converging with diverging-converging parts of the reaction chamber.

In addition to the reaction chamber, the microfluidic chip of the invention is configured to include one or more of a variety of components that will be present on any given device depending on its use. These components include, but are not limited to, sample inlet ports; sample introduction or collection modules; cell handling modules (for example, for cell lysis (including the microwave lysis of cells as described herein), cell removal, cell concentration, cell separation or capture, cell growth, etc.; separation modules, for example, for electrophoresis, gel filtration, ion exchange/affinity chromatography (capture and release) etc.; reaction modules for chemical or biological reactions or alteration of the sample, including amplification of the target analyte (for example, when the target analyte is nucleic acid, amplification techniques are useful.

All the previously described embodiments and aspects of the present invention have as a main objective to enhance the reaction rate between any target substances within a liquid medium and the particle surfaces suspended in the said liquid. An effective mixing, will indeed have a strong impact on the performance of any biochemical process such as the extraction or (and) detection of biomolecules for example (but not limited to) nucleic acids and proteins. Moreover, one key element of the disclosed magnetic particles handling concept is that the particles manipulation procedure can be readapted or adjusted in correspondence with the biochemical process in consideration.

Usually the surface of the magnetic particle is biochemically functionalized by specific ligands for the probing and manipulating of biomolecules and chemical substances using well-known techniques. For this, the magnetic particle surface comprises for example a functional group or a ligand that is capable of binding to a target molecule or to class of target molecules. Potential functional groups comprise but are not limited to carboxylic acids, hydroxamic acids, non-adhesive compounds, amines, isocyanates, and cyanides. Potential ligands comprise but are not limited to proteins, DNA, RNA, enzymes, hydrophobic materials, hydrophilic material, and antibodies. More generally, examples of ligands suitable for use in the present invention include, but are not limited to, molecules and macromolecules such as proteins and fragments of proteins, peptides and polypeptides, antibodies, receptors, aptamers, enzymes, substrates, substrate analogs, ribozymes, structural proteins, nucleic acids such as DNA and RNA and DNA/RNA hybrids, saccharides, lipids, various hydrophobic or hydrophillic substances, lipophilic materials, chemoattractants, enzymes, hormones, fibronectin, and the like. Such molecules and macromolecules may be naturally occurring or synthetic. The term ligand may also include larger entities such as cells, tissues, entire microorganisms, viruses, etc.

Using the so functionalized particles, the mixing and separation process of the present invention has particular utility in various laboratory and clinical procedures involving biospecific affinity binding reactions for separations. Such biospecific affinity binding reactions may be employed for the determination or isolation of a wide range of target substances in biological samples. Examples of target substances are, cells, cell components, cell subpopulations (both eukaryotic and prokaryotic), bacteria, viruses, parasites, antigens, specific antibodies, nucleic acid sequences and the like.

Moreover, the mixing and separation process of the present invention have particular use in detection procedures including, but not limited to polymerase chain reaction (PCR), real-time PCR, ligase chain reaction (LCR), strand displacement amplification (SDA), and nucleic acid sequence based amplification (NASBA).

Figure 3:
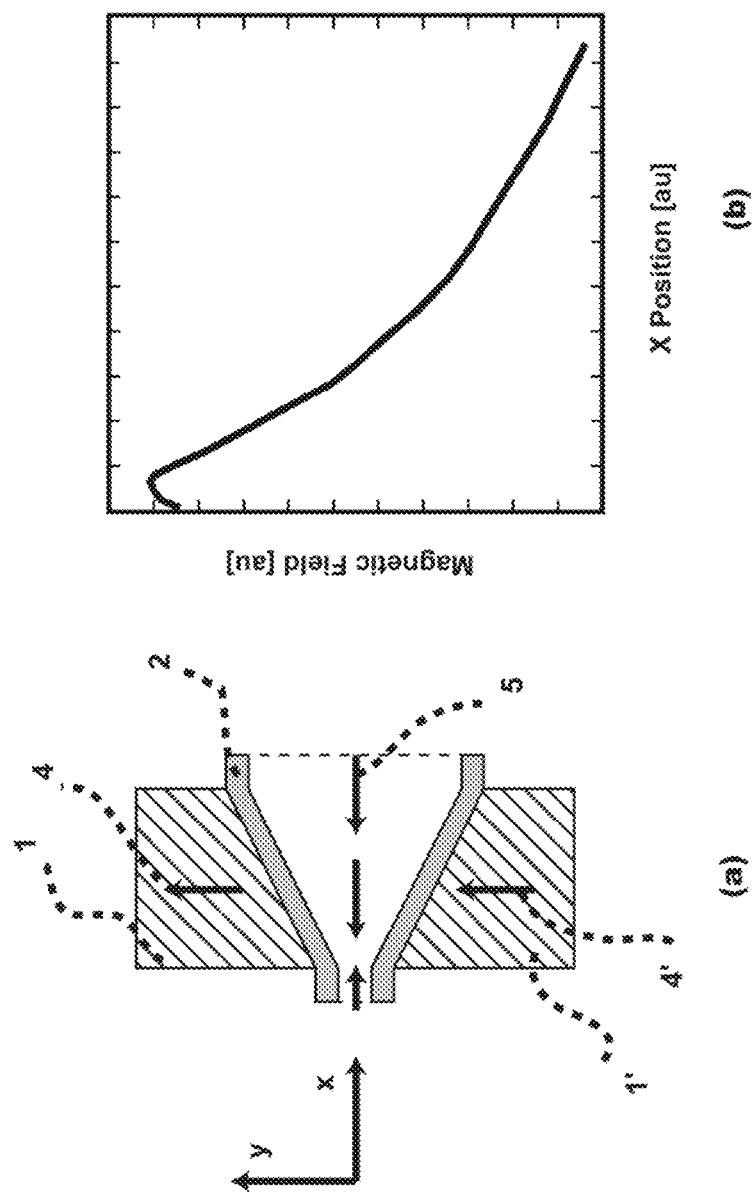
FIG. 3(a) shows a schematic representation of another preferred embodiment of the invention which includes in particular one couple of "diverging" magnetic poles and a reaction chamber that has a diverging cavity arranged co-divergently with the gap geometry.
FIG. 3(b) shows the magnetic field variation profile along the axis of the said magnetic poles.
Figure 4:
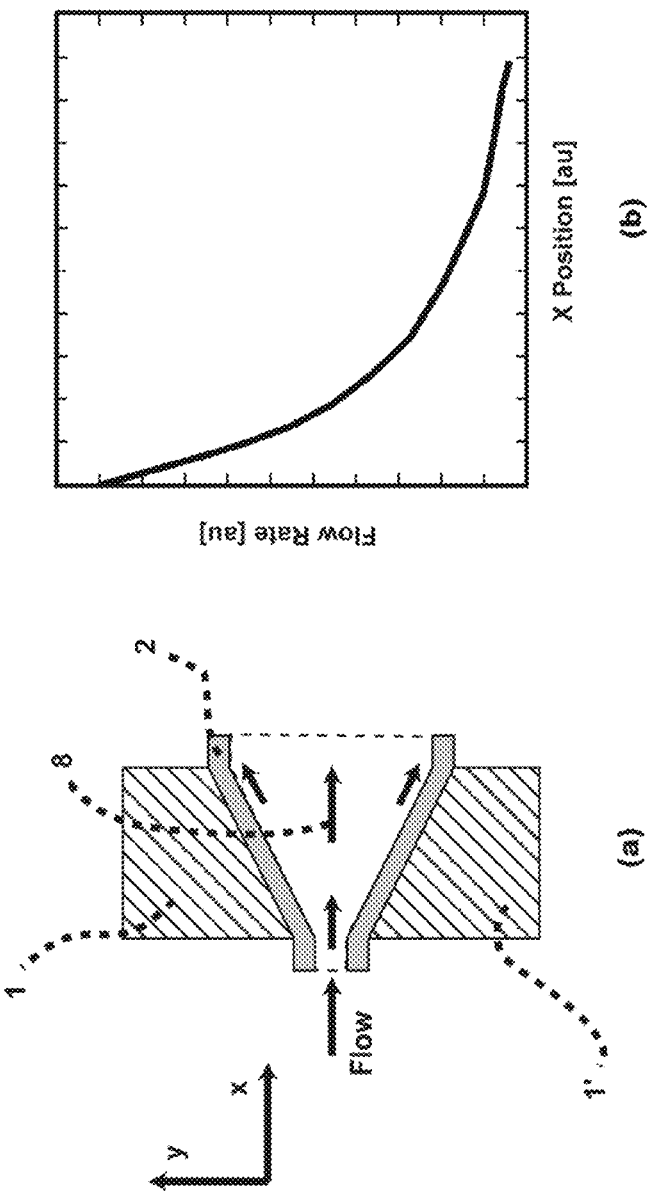
FIGS. 4(a) and (b) show the flow velocity profile and variation induced by the diverging reaction chamber geometry.
Figure 11:
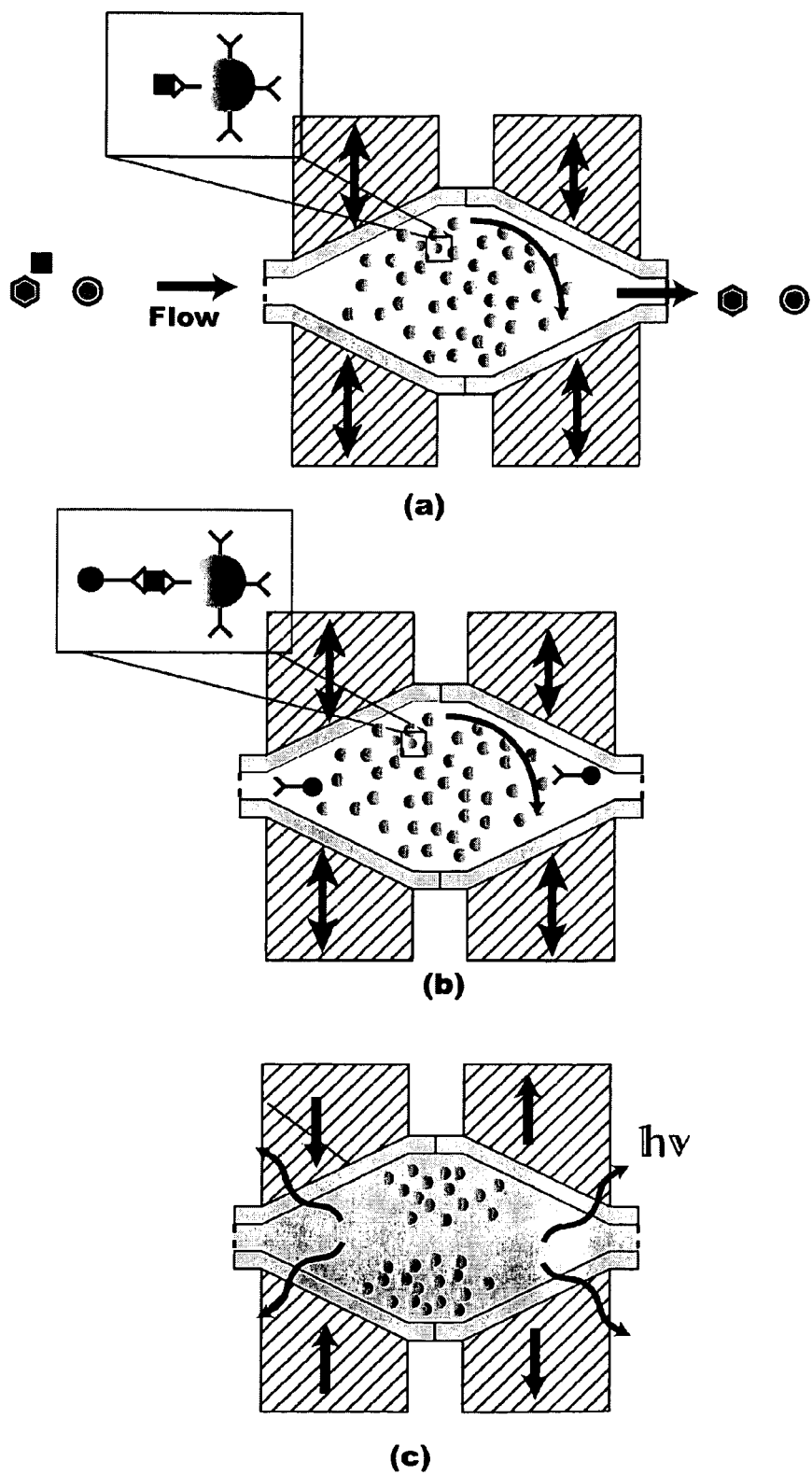
FIGS. 11(a) to (c) schematically represent a process of using the inventive mixing method and device for performing an assay in general and an immunoassay in particular.

An example of use of the disclosed magnetic particles handling and mixing devices/method is illustrated in FIG. 11. This Figure illustrates the different steps of a sandwich immunoassay where: (a) In a first step (FIG. 11(a)) the particles coated with specific capturing probes will be mixed to homogenously cover the reaction chamber as previously described in FIGS. 7 and 8. In this step the sample containing the target biomolecules is pushed with a liquid flow through the reaction chamber. For that purpose reaction chamber/magnetic pole "co-variation" geometries will assure (as shown in FIG. 3 and FIG. 4) the homogeneity of the mixing conditions of the magnetic particles with the liquid flow. All these conditions when tidily adjusted allow a strong capturing efficiency of the targets on the particles surfaces. (b) After a washing step, as described in FIG. 11(b), a defined volume (substantially equal to the volume of the reaction chamber) of a reagent containing detection probes is injected in the reaction chamber. In this case the particles can be again homogenously mixed with the surrounding medium allowing efficient capturing of the detection probe on the particle surfaces. (c) After a washing step, as described in FIG. 11(c) a defined volume (substantially equal to the volume of the reaction chamber) of a reagent detection substrate is injected in the reaction chamber. In this case the particles can be homogenously contacted and mixed with the surrounding medium allowing efficient interaction between the substrate and the detection probes on the particle surfaces. Contrary to classical immunoassay tests where the detection signal is mainly induced by diffusion, our mixing process allows a strong interaction between the detection substrate and the particles surfaces covering the whole reaction chamber volume. A large enhancement of the detection signal can be therefore generated in this way allowing the detection of low target molecules concentration within the starting sample (as blood or plasma). As shown in FIG. 11 (c), during the detection the particles can be drawn (separated) to the reaction chamber borders following the sequence of FIG. 7(b).

Figure 12:
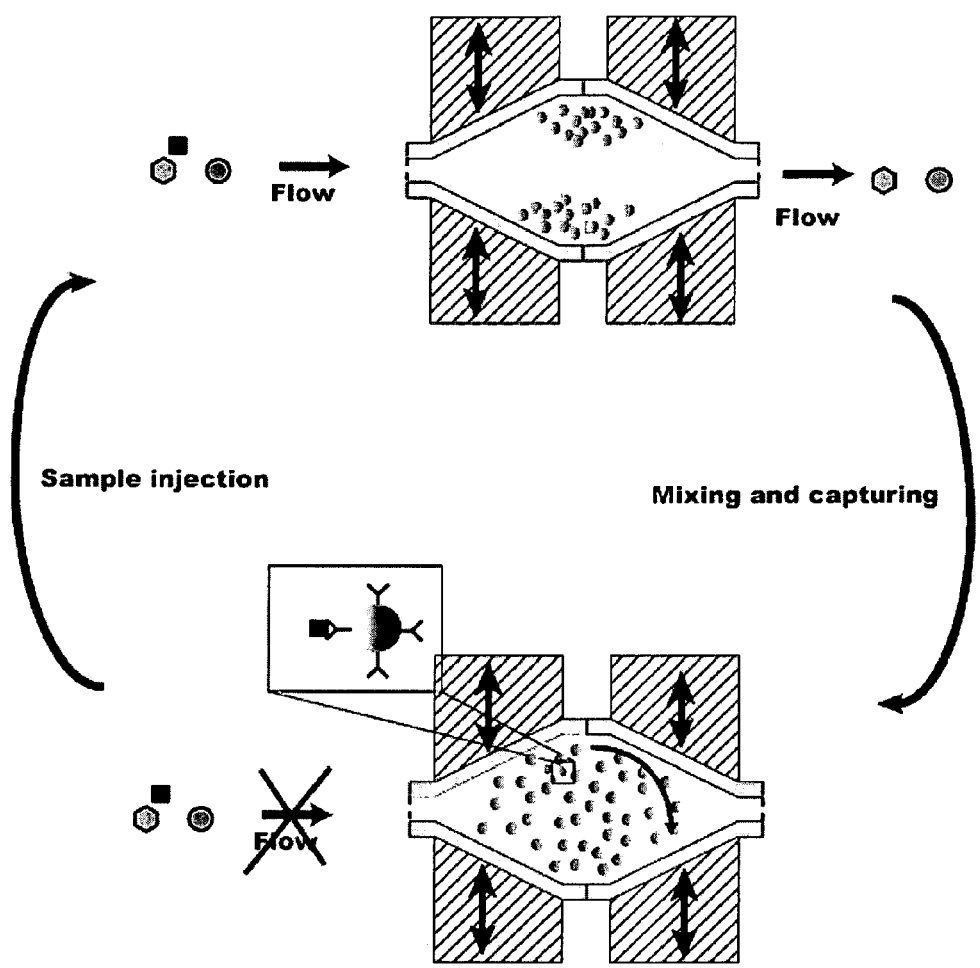
FIG. 12 schematically illustrates another embodiment of handling and mixing magnetic particles with the surrounding medium in a "pulsed-injection/mixing" mode.

In a different embodiment of the use of magnetic particles handling and mixing according to the invention, rather than having a flow-through for capturing targets from a large sample volume (as for instance described in the first step of the previous example 11(a)), a target concentration can be achieved in a more controlled way under a static (no-flow) condition. This embodiment, schematically illustrated in FIG. 12, is based on the use of the concept of "pulsed injection" (instead of continuous flow) of the sample in the reaction chamber followed by a homogenous mixing of the particles. More specifically, in a first step (FIG. 12, top) the particles are attracted to the reaction chamber walls (using the actuation sequence of FIG. 7(b)) and retained while a defined volume of the sample, that will not exceed the reaction chamber volume, is injected. In a second step (FIG. 12 bottom), the particles coated with specific capturing probe will be mixed to homogenously cover the reaction chamber as previously described in FIG. 8, but without any flow. After mixing of a defined time period, the particles will be attracted again to the reaction chamber walls and the new sample volume injected to the reaction and than mixed. This process will be repeated in sequential way until the full sample volume is mixed with the magnetic particles.

One of the advantages of such "pulsed-injection/mixing" mode is that one will avoid to deal with the constraints of handling magnetic particles in a flow-through condition which is actually very difficult to setup. Moreover, contrary to the flow-through case where the contact time is still relatively extremely short, the mixing time can be more easily controlled in a pulsed mode and adapted in correspondence with the target molecules and the final use.

The following examples further describe in detail the manner and process of using the present invention. The examples are to be considered as illustrative but not as limiting of this invention. All manipulations given in the examples are at ambient temperature unless otherwise indicated.

EXAMPLE 1 OF ACTUATION MECHANISM

Figure 7:
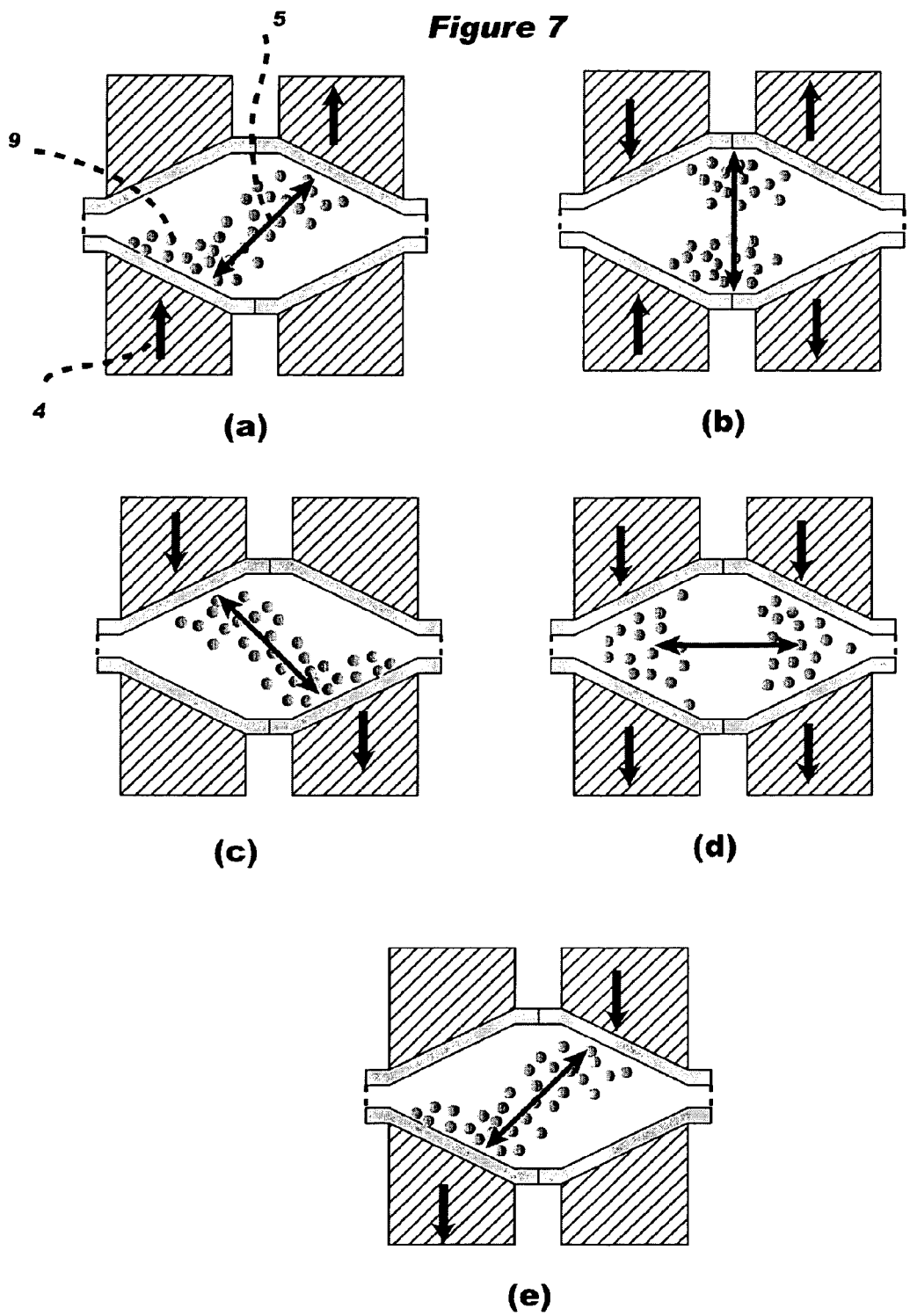
FIGS. 7(a) to (e) schematically represent, for the preferred embodiment of FIG. 6, the relative position and motion of the particles across the reaction chamber volume as a consequence of the actuation sequences of the electromagnetic poles using a magnetic field having a polarity and amplitude that vary with time.
Figure 8:
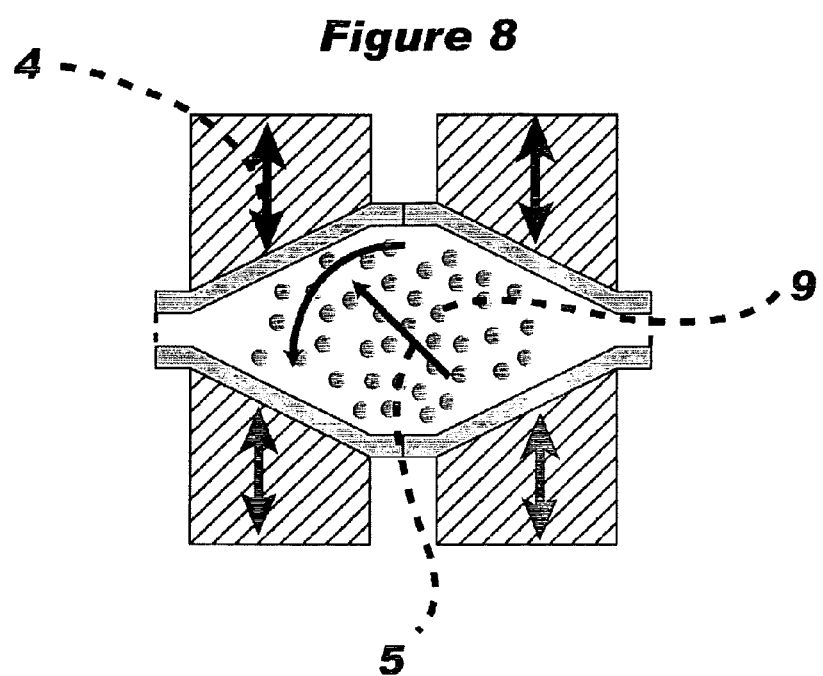
FIG. 8 schematically represents the desired effect obtained with the quadrupole embodiment according to the invention where the particles mixing and movement homogenously cover the whole reaction chamber volume.

The actuation sequences of FIG. 7, is an illustration on how the magnetic particles, while the magnetic poles are actuated using a time varied (amplitude and polarity) magnetic field, is used as a base sequence, can be moved following the combination of the magnetic field from each magnetic pole. During this movement the particles will substantially cover the whole reaction chamber volume as a fog of particles thereby assuring mixing. Although represented as "discontinuous" sequences, the sequences of the particles as shown in FIG. 7 can be achieved with a "rotating magnetic field" following the magnetic poles actuation sequences:

Pole 1 and 10': $B = B_0 \sin(ft)$

Pole 1' and 10: $B = B_0 \sin(ft + \pi/2)$ (3)

In equation (3) the base sequence actuation in each magnetic pole is an oscillating field while the actuation process is assured by a phase shift of $\pi/2$ between the diagonally coupled magnetic poles. In this configuration the base and the sequence actuation fields have the same frequency f.

In the actuation according to the sequences of equation (3), two particles regimes can be distinguished: a low frequency and high frequency regime.

At low frequency typically for f<5 Hz, the particles will rotate relatively "slowly" and the particles will move across the reaction volume producing typically the sequences as schematically shown in FIG. 7. The particularity of this regime is that the particles during their movement from one magnetic poles configuration to the other (see FIG. 7), the particles will have enough time to "aggregate" in longer magnetic chains. For frequencies higher than 1 Hz, the particles will exhibit fast and strong dynamics that covers substantially the whole (>90%) reaction volume. However, at this regime of a rotating magnetic field the particles still "relatively" aggregated.

Figure 13A:
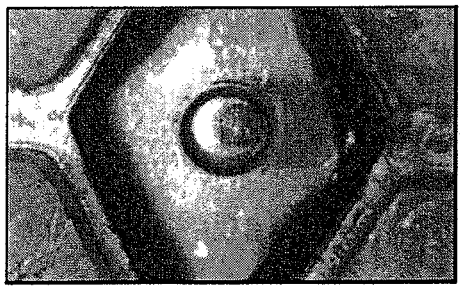
FIGS. 13 (a) and (b) illustrate different behavior of the magnetic particles under a "rotating magnetic field".

More disaggregated particle sate will be ultimately obtained at higher frequencies of the rotating field f>5 Hz. At this regime instead the particles behaviour is drastically different as the fast rotation of the magnetic particles will not give enough time for chain formation leading the particles chains to break down to smaller particles chain-like structures with a size that decreases with the field frequency. As a difference with the low-frequency regime, the sequence of FIG. 7 (b) will not be observed as the particles will not have time to extend along the diagonal of the reaction chamber. What happens at high frequency indeed is that the particles will be attracted and confined at the reaction chamber walls. FIG. 13(a) shows a video of the particles behaviour at high frequencies.

Figure 13B:
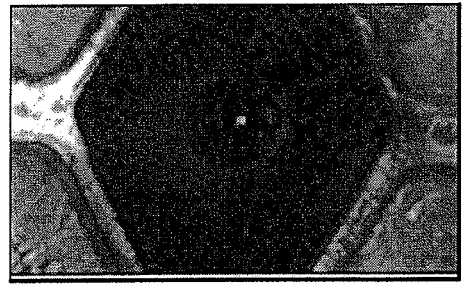

To overcome this problem, a finding of this invention is to reduce the amplitude while increasing the frequency of the applied rotating field in combination with the use of ferromagnetic particles. The reduction of the magnetic field amplitude indeed allows to expand the particles more over the reaction chamber volume due to reduction of the magnetic gradient forces and the repulsive dipolar forces between the rotating particles. However, as the reduction of the magnetic forces will slow down the particles movement, a higher frequency field is required to further propel the particles movement. At such high frequencies typically between superior to 20 Hz and preferably in the range of 100 Hz to 500 Hz, the use of ferromagnetic particles is key as the "magnetic anisotropy" of these particles leads them to move and follow the field variations. FIG. 13(b), shows the homogenous coverage of the particles in the reaction chamber obtained under a high rotating frequencies (around 300 Hz). During this mixing, the particles strongly move across the reaction chamber allowing thereby strong and efficient mixing.

It is important to point out here that the frequencies values given in this example are typical values just for indication, obtained with specific particles used in experiments (MagNA Pure LC particles from Roche Diagnostics). The use of other particles types will certainly affect the frequencies limits of different particles regimes and behaviours as described before.

EXAMPLE 2 OF ACTUATION MECHANISM

Equation (4) describes another actuation sequences to achieve mixing according to the invention.

Pole 1 and 10': $B = B_0 \sin(f_1 t) \sin(f_2 t)$

Pole 1' and 10: $B = B_0 \sin(f_1 t) \sin(f_2 t + \pi/2)$ (4)

In this sequence indeed the first oscillation component ($\sin(f_1 t)$) is nothing more than the base actuation field at a frequency $f_1$ of the magnetic poles while the second term defines the actuation sequence that moves the "fog" of particles in rotation form with a frequency $f_2$. The sequence of equation (4) allows in particular to solve the previously reported (in the Example 1) agglomeration of particles in a low frequency rotating field of equation (3). For instance by rotating the particles as a frequency $f_2=1$ Hz, the particles chains will break down due to the fast oscillation of the base field $f_1 > 10$ Hz.

EXAMPLE 3 OF ACTUATION MECHANISM

Equation (5) describes another actuation sequence to achieve mixing according to the invention, where the frequency of the rotating magnetic field of equation (1) of equation is "modulated".

$$f = f_0 + f_1 \sin(\Omega t) \quad (5)$$

The finding is that modulating the frequency between a low frequencies regime and the high frequencies regime assures thereby efficient mixing. By appropriate choice of the modulating frequency ($\Omega$), when can balance between the two regimes: homogenous mixing with agglomerations at lower frequencies and the "inhomogeneous" mixing with fog particles structure at higher frequencies. This way of "modulating" the frequency of the rotating field is particularly important for highly viscous liquids where homogenous mixing is difficult to achieve by only increasing the oscillating frequency as described in Example 1.

It is obvious for skilled persons that the frequency modulation can be done by other forms, as for instance a "square" signal where one switch between one high frequency value and a low frequency one. Each value can be maintained for a certain time that depends essentially on the liquid viscosity, to assure an homogenous mixing.

It is worth to emphasize here again that the particles in use are preferably ferromagnetic to allow the particles to move and rotate at high frequency.

EXAMPLE 4 OF ACTUATION MECHANISM

Although the previous examples are based on using "rotating magnetic field", linear actuation sequence of particles fog can be also used to mix and reach an homogenous state. Typical example of that linear actuation mode can be achieved by first moving the particles to the out border as shown in FIG. 7(b) using the actuation sequence:

Pole 1 and 1': $B = B_0 \sin(\omega t)$

Pole 10 and 10': $B = B_0 \sin(\omega t + \pi)$ \quad (6)

At this stage the particles can be moved to the left corner (narrow part) of the reaction chamber by the sequence:

Pole 1 and 1': $B = B_0 \sin(\omega t)$

Pole 10 and 10': $B = B_0 \sin(\omega t + \pi/2)$ \quad (7)

By symmetry a displacement toward the right corner (narrow part) of the reaction chamber can be achieved by the sequence:

Pole 1 and 1': $B = B_0 \sin(\omega t + \pi/2)$

Pole 10 and 10': $B = B_0 \sin(\omega t)$ \quad (8)

A sequential shift between the previous three configuration following the sequences: (6)→(7)→(6)→(8) at a determined rate, one can achieve an homogenous mixing over the time.

In practice, better mixing processes are achieved not through only a rotating or a linear mode, but usually a mix of both modes is preferred.

Herein in these examples the choice of a "sinusoidal" field as base actuation is only for it is practical analytical formulation with an equation. Within the invention scope, more complex actuation "base sequences" having polarity and intensity that vary in time will lead to the same effects.

EXAMPLE 5 OF USE OF THE MIXING CONCEPT AND DEVICE

In this example the disclosed magnetic particles device and method are used for DNA extraction from bacteria (E-coli) culture with an inserted plasmid. For the extraction, MagNA Pure LC kit from Roche Diagnostics (Switzerland) is used. A particularity of this kit is that the magnetic particles exhibit a ferromagnetic response with a coercive field of around 200 Oe.

For the sample preparation, 200 µl of the bacteria culture in PBS with a concentration of around $2 \times 10^8$ cells/ml are mixed with: (a) 400 µl of lysis binding buffer, (b) 100 µl of isopropanol, and (c) 100 µl of Proteinase-K. The total extraction volume is therefore 800 µl.

For the assay, a microfluidic chip with the layout of FIG. 11 is used. The reaction chamber in this chip has the following dimensions: H=0.25 mm, L=0.5 mm and a depth of 1 mm. The total volume of the reaction chamber is therefore around 25 µl. In this reaction chamber around 50 µl of the glass particles from the kit is separated and retained in the reaction chamber.

The samples and reagents processing through the chip is performed following the previously described "pulse-injection" mode and where the particles are homogenously mixed over the reaction chamber over a period of 2 s followed by a separation and liquid injection of around 1 s. Around 3 seconds are necessary to process 25 µl of the sample volume witch is equivalent to processing flow rate of 0.5 ml/min.

The washing step is performed using the three washing reagents of the kit with 300 µl volume of each. The washing is performed by combining both the flow-through mode and "pulse-injection" mode. Less than 2 minutes are necessary to perform all the necessary washing steps. For the DNA elution, a volume of the elution buffer from the kit substantially equal to the reaction chamber volume (~30 µl) and homogenously mixed for around 3 minutes.

To determine the homogenous mixing benefits, the extraction performance is compared with the standard manual extraction (as a reference) and the non-homogenous mixing under a high frequency rotating magnetic field as described in example 1 and shown in FIG. 13(a). For the performance of DNA extraction experiments we use the optical absorbance, with the following results:

|  | Total DNA amount (µg) | Purity (OD 260/280) |
|---|---|---|
| Manual extraction | 6 | 1.7 |
| Homogenous mixing | 5.5 | 1.9 |
| Non-homogenous mixing | 1.2 | 1.6 |

From these results one can see the strong impact of the proposed magnetic particles mixing effect in enhancing the affinity binding between the particles and the target molecule (DNA) in the sample. In fact, while the manual extraction takes around 20 minutes to be performed around 8 minutes are necessary for full extraction using the disclosed homogenous mixing method and device. Moreover, in the manual extraction around 100 μl of particles suspension is used while only 50 μl is used in the microfluidic homogenous mixing. Taking in consideration the relatively large amount of DNA that can be purified (up to 10 μg) in a small reaction chamber volume (25 μl) with the disclosed homogenous mixing as disclosed herein, is clear expression of the large available surface of particles during the mixing demonstrating the effective particles desegregation and mixing during the assay. Another demonstration of the particles homogenous mixing is the low performance obtained by non-homogenous mixing.

EXAMPLE 6 OF USE OF THE MIXING CONCEPT AND DEVICE

In this example the disclosed magnetic particles device and method are used for DNA extraction from human whole blood. For the extraction, MagNA Pure LC kit II from Roche Diagnostics (Switzerland) is used with the same process and protocol as Example 4.

The extraction results show a yield between 4-5 μg of DNA with an OD value between >1.7. This example, demonstrate the efficient DNA extraction of the disclosed mixing method from a complex sample like whole blood.

Those skilled in the art will appreciate that various adaptations and modifications of the just-described preferred embodiments can be configured without departing from the scope and spirit of the invention. Therefore, it is to be understood that, within the scope of the appended claims, the invention may be practiced otherwise than as specifically described herein.

What is claimed is:

1. A device for mixing magnetic particles in a surrounding liquid medium and separating magnetic particles from a liquid medium, comprising:
   (a) at least two magnetic poles facing each other across a gap, the facing poles diverging continuously from a narrow end of the gap to a large end of the gap, the poles being part of an electromagnetic circuit arranged to provide a magnetic field gradient in the said gap region;
   (b) a reaction chamber that is a part of a microfluidic network for containing the magnetic particles in suspension and placed in the gap of the magnetic poles, wherein the reaction chamber comprises a cavity extending between its ends along said gap and having at least one diverging part arranged co-divergently in the diverging gap between the poles, wherein the narrow and the large ends of the reaction chamber are connected respectively to an inlet and an outlet for delivering liquids into and from the reaction chamber.

2. The device according to claim 1, wherein each of the magnetic poles is actuated with magnetic field sequences having polarity and amplitude that vary in time to induce continuous time variations of the position of the magnetic field gradient maxima across the reaction chamber, causing thereby the particles in use to be in relative translational and rotational motion as a fog of particles covering substantially the whole reaction chamber volume.

3. The device according to claim 1, wherein the reaction chamber comprises a microchannel.

4. The device according to claim 1, wherein the ratio of the depth (H) of the large end to the length (L) of the diverging part of the reaction chamber between 0.1 to 1.

5. The device according to claim 2, wherein the time-varied magnetic sequence has substantially a rectangular, sinusoidal, saw-tooth, asymmetrical triangular, or symmetric triangular form; or any combination of said forms.

6. The device according to claim 5, wherein the pulsation or oscillation frequency of the magnetic field is between 0.1 to 1000 cycles per second.

7. The device according to claim 1, wherein the particles are ferromagnetic with a coercive field between 50 to 10,000 Oe.

8. The device of according to claim 7, wherein the particles are designed to selectively bind with at least one target molecule or with particles carried in the reaction chamber by a fluid flow.

9. The device according to claim 8, wherein fluid flows through the reaction chamber as an oscillating flow.

10. The device according to claim 1, further comprising:
    (a) a quadrupole configuration of magnetic poles comprising
       i) a first pair of magnetic poles facing each other forming a first diverging gap; and
       (ii) a second pair of magnetic poles facing each other and forming a second diverging gap, with the large ends of the diverging gaps of the first and second pairs of poles facing one another; and
    (b) the reaction chamber comprises a cavity with diverging parts, the large ends of the diverging parts facing one another; wherein
    (c) the diverging parts of the reaction chamber are arranged co-divergently in the diverging gaps between the poles.

11. A microfluidic chip comprising:
    (a) a reaction chamber that is a part of a microfluidic network for containing particles in suspension, having at least one cavity with diverging and converging parts;
    (b) an opening placed on both sides of the reaction chamber to receive magnetic poles that are part of an external magnetic circuit, the magnetic poles geometrically arranged in the openings to be co-diverging and co-converging with the diverging and converging parts of the reaction chamber;
    (c) microfluidic channels in the chip that provide inlets and outlets at the sides of the reaction chamber.

12. The microfluidic chip according to claim 11, wherein the volume of the reaction chamber is between 0.1 μl to 500 μl.

* * * * *